(12) United States Patent
Waters et al.

(10) Patent No.: US 10,527,453 B2
(45) Date of Patent: Jan. 7, 2020

(54) SYSTEM OF POWER-SAVING IN MEMS SENSOR APPLICATIONS

(71) Applicant: Texas Instruments Incorporated, Dallas, TX (US)

(72) Inventors: Deric Wayne Waters, Dallas, TX (US); Jayawardan Janardhanan, Issaquah, WA (US); Saket Thukral, San Diego, CA (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 106 days.

(21) Appl. No.: 15/845,984

(22) Filed: Dec. 18, 2017

(65) Prior Publication Data

US 2018/0100749 A1   Apr. 12, 2018

Related U.S. Application Data

(60) Division of application No. 14/830,206, filed on Aug. 19, 2015, now Pat. No. 9,846,054, which is a division (Continued)

(51) Int. Cl.
*G01C 23/00* (2006.01)
*G01D 18/00* (2006.01)
(Continued)

(52) U.S. Cl.
CPC .............. *G01C 23/00* (2013.01); *G01C 21/16* (2013.01); *G01D 18/00* (2013.01); *A61B 5/00* (2013.01);

(Continued)

(58) Field of Classification Search
CPC .......... A63F 13/06; A63F 13/10; A63F 13/24; A63F 13/285; A63F 13/428;
(Continued)

(56) References Cited

U.S. PATENT DOCUMENTS 7,558,622 B2 * 7/2009 Tran ..................... A61B 5/0022
600/509
8,362,949 B2   1/2013 Yang et al.
(Continued)

OTHER PUBLICATIONS

Patent Prosecution History for U.S. Appl. No. 14/830,206 from Aug. 19, 2015 to Nov. 30, 2017 (239 pages).

(Continued)

*Primary Examiner* — Behrang Badii
(74) *Attorney, Agent, or Firm* — Brian D. Graham; Charles A. Brill; Frank D. Cimino

(57) ABSTRACT

A system comprises a plurality of sensors, a sensor processor, and a sampling rate engine. The sensor processor is coupled to an output of each sensor of the plurality of sensors. The sensor processor estimates user dynamics in response to a first output signal of a first sensor of the plurality of sensors. The sampling rate engine is coupled to an output of the sensor processor. The sampling rate engine determines a sampling rate value of a second sensor of the plurality of sensors in response to a user dynamics value from the sensor processor. The second sensor comprises a selectable sampling rate. The selectable sampling rate is configured in response to the sampling rate value determined by the sampling rate engine.

7 Claims, 8 Drawing Sheets

Related U.S. Application Data of application No. 14/830,170, filed on Aug. 19, 2015, now Pat. No. 9,677,905, which is a continuation of application No. 14/039,785, filed on Sep. 27, 2013, now Pat. No. 9,140,590, which is a continuation-in-part of application No. 13/023,987, filed on Feb. 9, 2011, now Pat. No. 8,612,146.

(51) Int. Cl.

| | | |
|---|---|---|
| *G01C 21/16* | (2006.01) | |
| *A61B 8/00* | (2006.01) | |
| *A61B 8/08* | (2006.01) | |
| *G01S 19/48* | (2010.01) | |
| *A61B 5/00* | (2006.01) | |
| *G01S 19/47* | (2010.01) | |
| *G01S 19/49* | (2010.01) | |
| *G08B 21/04* | (2006.01) | |
| *G01S 19/34* | (2010.01) | |
| *G06F 19/00* | (2018.01) | |
| *A61B 5/053* | (2006.01) | |
| *H04N 5/232* | (2006.01) | |
| *H04N 7/18* | (2006.01) | |
| *G06F 1/32* | (2019.01) | |
| *G06K 9/62* | (2006.01) | |
| *A61B 5/145* | (2006.01) | |
| *G16H 40/40* | (2018.01) | |
| *G16H 20/30* | (2018.01) | |
| *G16H 15/00* | (2018.01) | |

(52) U.S. Cl.
CPC ........... *A61B 5/0006* (2013.01); *A61B 5/0022* (2013.01); *A61B 5/0537* (2013.01); *A61B 5/145* (2013.01); *A61B 5/14532* (2013.01); *A61B 5/72* (2013.01); *A61B 8/488* (2013.01); *A61B 8/565* (2013.01); *G01S 19/34* (2013.01); *G01S 19/47* (2013.01); *G01S 19/48* (2013.01); *G01S 19/49* (2013.01); *G06F 1/32* (2013.01); *G06F 19/3418* (2013.01); *G06K 9/62* (2013.01); *G08B 21/0423* (2013.01); *G16H 15/00* (2018.01); *G16H 20/30* (2018.01); *G16H 40/40* (2018.01); *H04N 5/232* (2013.01); *H04N 5/23241* (2013.01); *H04N 7/18* (2013.01)

(58) Field of Classification Search
CPC .. A63F 13/214; A63F 13/2145; A63F 13/235; A63F 13/92; A63F 9/24; A63F 13/211; A63F 13/213; A61B 5/14532; A61B 5/145; A61B 5/00; A61B 5/72; A61B 5/725; A61B 5/7225; A61B 5/742; A01G 25/167; A01G 25/16; G08B 13/196; G08B 25/08; A61H 19/34; A61H 19/44; A61H 23/00; A61H 19/30; G05B 19/05; H04W 4/90; H04M 11/04; G06F 3/011; G06F 3/0325; G06F 3/0346; G06F 3/033; G06F 3/0362; G06F 3/04815; G06F 19/3481; G01P 3/38; G01P 15/00; G01C 21/16; G01D 18/00; A43B 3/0005; A43B 5/16; A43B 5/001; A63B 24/00; A63B 24/0021; A63B 71/0622; A63B 71/0669; G06Q 10/10

See application file for complete search history.

(56) References Cited

U.S. PATENT DOCUMENTS

| | | |
|---|---|---|
| 8,676,528 B2 | 3/2014 | Almalki et al. |
| 8,949,070 B1 | 2/2015 | Kahn et al. |
| 2007/0072680 A1* | 3/2007 | Ikeda ..................... A63F 13/06 463/43 |
| 2007/0219751 A1* | 9/2007 | Huang ..................... H04Q 9/00 702/187 |
| 2009/0069987 A1 | 3/2009 | Omelchenko et al. |
| 2009/0326851 A1 | 12/2009 | Tanenhaus |
| 2012/0150294 A1 | 6/2012 | Weinberg et al. |
| 2012/0326922 A1* | 12/2012 | Yang ..................... G01S 19/34 342/357.3 |
| 2014/0358473 A1* | 12/2014 | Goel ..................... A61B 5/1118 702/141 |
| 2014/0368688 A1* | 12/2014 | Archibald .......... H04N 5/23241 348/222.1 |
| 2017/0027483 A1* | 2/2017 | Budiman ........... A61B 5/14532 |

OTHER PUBLICATIONS

Patent Prosecution History for U.S. Appl. No. 14/830,170 from Aug. 19, 2015 to May 25, 2017 (118 pages).
Patent Prosecution History for U.S. Appl. No. 14/039,785 from Sep. 27, 2013 to Sep. 3, 2015 (159 pages).
Patent Prosecution History for U.S. Appl. No. 13/023,987 from Feb. 9, 2011 to Nov. 27, 2013 (134 pages).

* cited by examiner

SYSTEM OF POWER-SAVING IN MEMS SENSOR APPLICATIONS

CROSS-REFERENCE TO RELATED APPLICATIONS

This application is a Divisional of U.S. patent application Ser. No. 14/830,206 filed on Aug. 19, 2015, which is a Divisional of U.S. patent application Ser. No. 14/039,785 filed on Sep. 27, 2013, which is a continuation-in-part of and claims priority to U.S. patent application Ser. No. 13/023,987 filed Feb. 9, 2011, all of which are hereby incorporated by reference as if reproduced in full below.

TECHNICAL FIELD

The present invention relates to micro-electromechanical system (MEMS) sensors and, in particular to systems and methods for power savings in MEMS sensor applications.

BACKGROUND

Some navigation systems are based on signals received from orbiting satellites, such as the Global Positioning System (GPS) satellites. Performance of such systems degrades if the receiver does not have a direct line-of-sight to the orbiting satellites. Performance of such satellite-based systems degrades if the signal from the satellite is blocked such as by buildings, mountains, etc. Using MEMS sensors to augment such satellite-based navigation systems is a way to mitigate against signal degradation or loss in satellite-based navigation systems.

MEMS sensors used in consumer electronics devices, smartphones or tablet computers, for example, typically have a tradeoff between sampling rate and power consumed by the sensor. Further, depending on the application of the sensor output, performance may be reflected in the sampling rate. Further, in handheld or other battery-powered device power budgets may be constrained. Thus, any system or method that can reduce power consumption without noticeably degrading performance provides a competitive advantage in the marketplace.

BRIEF DESCRIPTION OF THE DRAWINGS

For a detailed description of exemplary embodiments of the invention, reference will now be made to the accompanying drawings in which.

NOTATION AND NOMENCLATURE

Certain terms are used throughout the following description and claims to refer to particular system components. As one skilled in the art will appreciate, companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect, direct, optical or wireless electrical connection. Thus, if a first device couples to a second device, that connection may be through a direct electrical connection, through an indirect electrical connection via other devices and connections, through an optical electrical connection, or through a wireless electrical connection.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Figure 1:
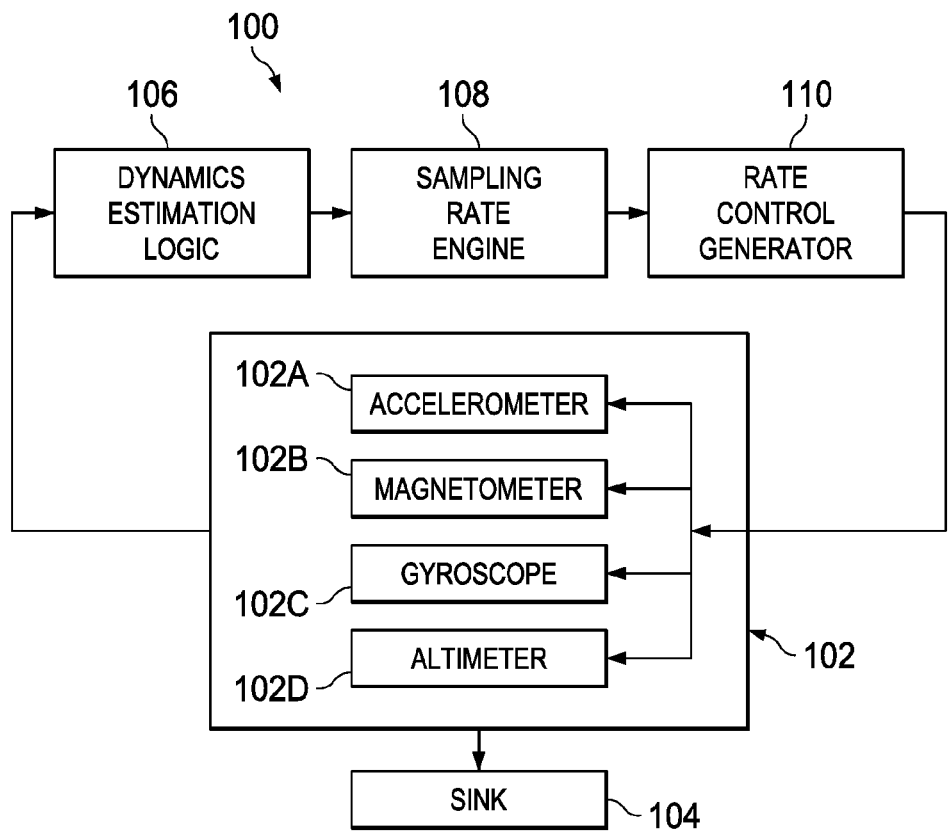
FIG. 1 shows a block diagram of a system in accordance with an embodiment of the disclosure.

Refer now to FIG. 1 illustrating a block diagram of a system 100 for adaptively controlling MEMS sensor sampling rates in accordance with at least some embodiments of the disclosure. System 100 may comprise a portion of an end-user device such as a Tablet computer, smartphone, vehicular navigation system or the like. The principles disclosed herein are not limited to particular end-user devices.

System 100 includes a plurality of sensors 102 which may comprise, for example, an accelerometer 102A, a magnetometer (or, equivalently, encompass) 102B, a gyroscope 102C and altimeter 102D. One or more of the plurality of sensors 102 may provide signals indicative of the respective physical parameters to an application or hardware device within an end-user device coupled to sensors 102. Sink 104 comprises any such hardware device or application that uses signals from at least one of the plurality of sensors 102. System 100 also includes dynamics estimation logic 106 which also receives output signals from at least one of the plurality of sensors 102, sampling rate engine 108 which receives the output of dynamic estimation logic 106 to generate a sensor sampling rate for the sensor or sensors to be controlled and rate control generator 110 which receives the sampling rate and generates a signal to feed back to the sensor or sensors under control. In this respect, in accordance with the principles herein, in at least some embodiments, the sensors being controlled need not be the same sensors used to estimate dynamics. Further, the rate control generator may, in at least some embodiments, provide different sampling rates for each sensor being controlled.

Considering first dynamics estimation logic 106, based on the output signals from the plurality of sensors, dynamics estimation logic 106 determines if user dynamics associated with the end user device is high or low. In at least some embodiments, the determination may be made using the output of one of the plurality of sensors 102. Alternatively, in other embodiments the determination may be made using signals from two or more sensors. For example, dynamics estimation logic 106 may receive acceleration value signals from accelerometer 102A. In some embodiments, accelerometer 102A comprises a single axis accelerometer while in other embodiments accelerometer 102A comprises a multi-axis accelerometer. For example, the accelerometer in some embodiments comprises a 3-axis accelerometer. Accordingly, in a single axis accelerator embodiment, dynamics estimation logic 106 may determine the acceleration that the end-user device is experiencing along the single accelerometer axis. In at least some embodiments including a single-axis accelerometer, if, for example, the acceleration value indicated by the accelerometer is below a predetermined value, dynamics estimation logic 106 may determine that the user dynamics are low, and signal sampling rate engine 108 accordingly. In yet other embodiments comprising a single-axis accelerometer, dynamics estimation logic 106 may comprise a plurality of predetermined acceleration levels, and generate a signal to sampling rate engine 108 in accordance with a comparison of the acceleration values received from accelerometer 102A and each of the plurality of acceleration levels. In other words, as user dynamics, represented by acceleration values from the accelerometer fall below predetermined acceleration levels, dynamics estimation logic 106 signals sampling rate generator 108 accordingly, as described further below. Additionally, as previously described, in at least some embodiments, accelerometer 102A may comprise a multi-axis accelerometer wherein dynamics estimation logic 106 receives an acceleration value for each of the axes of the accelerometer. In such embodiments, dynamics estimation logic 106 may, in at least some embodiments, determine user dynamics based on the largest acceleration value of the components of the acceleration along each of the accelerometer axes by comparing the largest component with a predetermined acceleration level, similar to embodiments using a single-axis accelerometer. Likewise, in embodiments of dynamic estimation logic 106 comprising a plurality of predetermined acceleration levels, the largest component of the acceleration from the multi-axis accelerometer may be compared with each of the plurality of acceleration levels and the corresponding signal provided to sampling rate engine 108. Alternatively, in yet other embodiments, dynamics estimation logic 106 may compute from the accelerations for each of the axes, the magnitude of the acceleration representing the user dynamics. Recall that acceleration is a vector quantity and the acceleration values for each of the axes in a multi-axis accelerometer correspond to the components of the acceleration experienced by the accelerometer along the direction corresponding to each of the axes. The magnitude of the acceleration is a scalar value formed from the components of acceleration vector. The computation of the magnitude of a vector from the values of the components thereof would be readily know to those of ordinary skill in the art. The magnitude of the acceleration may then be used, in at least some embodiments, by dynamics estimation logic 106 to compare against a predetermined acceleration level in, or against a plurality of such levels, as in the single-axis embodiment described above. In addition to the magnitude of the acceleration, other metrics may be used. Examples of such other metrics are described in the related U.S. patent application Ser. No. 13/023987 for "ACCELEROMETER-AIDED GYROSCOPE" which is hereby incorporated by reference herein as if set forth in its entirety. One such exemplary metric is the magnitude of the acceleration adjusted for the acceleration of gravity. Another exemplary metric is the change in the sensor output (e.g. acceleration, angular rate, magnetic field intensity, pressure), if the device has low dynamics then it will see less change in the sensor output (e.g. the constant acceleration of gravity), but changes in the sensor output indicate higher dynamics.

Similar to accelerometer 102A, dynamics estimation logic 106 may also receive signals from magnetometer 102B, gyroscope 102C and altimeter 102D that are indicative of user dynamics. For example, signals from magnetometer 102B may indicate that an end-user device is undergoing no or otherwise slow rotation. Dynamics estimation logic 106 may determine, for example, that the rotation rate signaled by the magnetometer is below a predetermined rotation rate value, and further signal sampling rate engine 108 accordingly. Similarly, dynamics estimation logic 106 may compare rotation rates from magnetometer 102B with a plurality of predetermined rotation rate levels, and signal sampling rate engine 108 to generate sampling rates based on the level just exceeding the rotation rate obtained from the output of magnetometer 102B. Signals from gyroscope 102C representative of the orientation of an end-user device such as a smartphone, vehicle navigation system may be similarly used by dynamics estimation logic 106. In accordance with some embodiments, the gyroscope 102C comprises a single axis gyroscope while, in other embodiments, the gyroscope 102C comprises a multi-axis gyroscope. For example, the gyroscope 102C in some embodiments comprises a 3-axis gyroscope. Signals provided by gyroscope 102C to dynamics estimation logic 106 may be indicative of changes in orientation of an end-user device relative to the axes of the gyroscope. The rate of change of these signals may be determined by dynamics estimation logic 106 which may then further be used to determine user dynamics, in particular when user dynamics are low. For example, similarly to the magnitude of an acceleration vector, a magnitude of a rotation rate vector may be computed by dynamics estimation logic 106, and compared against a predetermined rotation rate level, or alternatively, against a plurality of predetermined levels. Based on the outcome of the comparison, dynamics estimation logic 106 signals sampling rate engine 108 accordingly. Note that, in at least dome embodiments, the monitoring of user dynamics may be continuous and dynamics estimation logic 106 may send signals to restore a sampling rate to a high value based on increasing user dynamics. Further, as described in conjunction with FIGS. 5-8 below, a sensor sampling rate may be reduced for a predetermined length of time whereby dynamics estimation logic 106 may send signals to restore a sampling rate after expiry of the time interval. Also, in at least some embodiments, dynamics estimation logic 106 may include a hysteresis whereby, on detecting low user dynamics, a delay is introduced before dynamics estimation logic 106 sends a signal to reduce a sensor sampling rate. And, in at least some embodiments, a signal to reduce sampling rates may be indicative of a zero sampling rate; that is, a signal to turn off a particular sensor or, alternatively switch to a low-power mode.

Sampling rate engine 108 determines a sampling rate for one or more of the plurality of sensors 102 based on the signal indicative of user dynamics received from dynamics estimation logic 106. In at least some embodiments, the sampling rates may be different for each of the sensors comprising the plurality of sensors 102. Further, in at least some embodiments, the choice of sampling rates may be binary, based on an estimate of user dynamics being above or below a predetermined level, as discussed above. In other embodiments, the sampling rate may be established with a finer granularity based on the estimate of the dynamics falling within a predetermined set of ranges of values, in accordance with at least some embodiments as also described above.

Sampling rate engine 108, in at least some embodiments may determine a sampling rate for each sensor of the plurality of sensors 102 based on a maximum sampling rate specification for the respective sensor and a corresponding signal indicative of user dynamics from dynamics estimation logic 106. For example, in at least some embodiments, sampling rate engine 108 may scale the maximum sampling rate for a sensor in proportion to the corresponding dynamics estimation level communicated by the signal from dynamics estimation logic 106. Further, in at least some embodiments, sampling rate engine 108 may determine a sampling rate for a particular sensor based on, for example, performing a calibration of the sensor or a requested override of any sampling rate reduction, as described further below.

Figure 2:
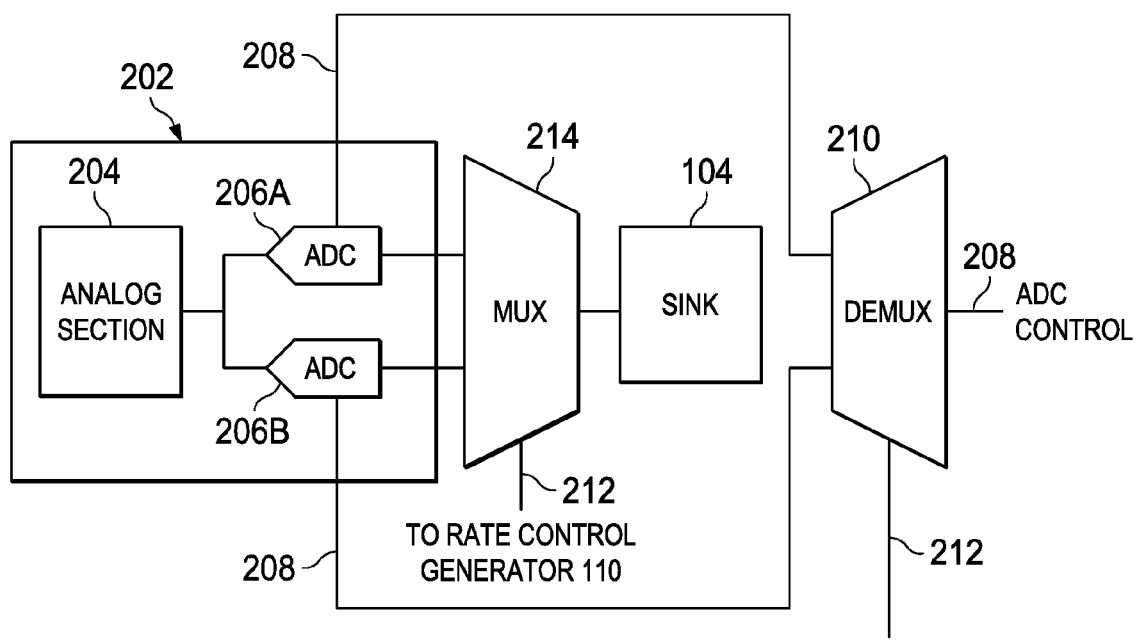
FIG. 2 shows a block diagram of a sensor in accordance with an embodiment of the disclosure.
Figure 3:
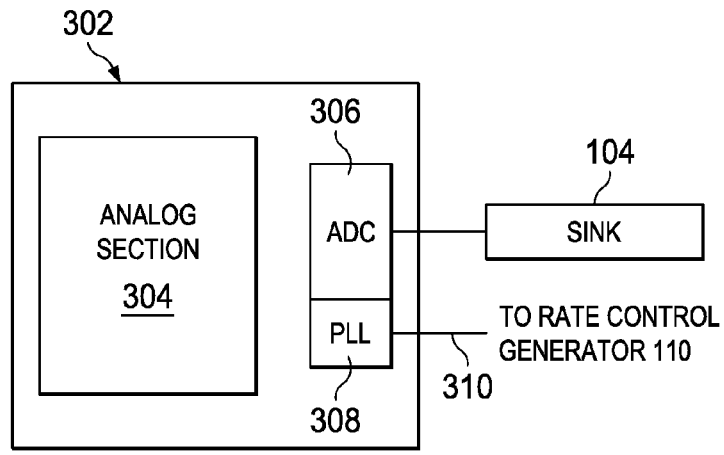
FIG. 3 shows a block diagram of a sensor in accordance with another embodiment of the disclosure

The sampling rate from sampling rate engine 108 is input to rate control generator 110. Rate control generator 110 maps the sampling rate to a control value appropriate to the sensor whose sampling rate is to be set in response to a change in user dynamics. For example, as previously described, in at least some embodiments, sampling rate control may be binary, in which case, a sensor sampling rate may be switched between a high, or maximum value appropriate to high user dynamics, and a low value suitable to low user dynamics. Such binary control may be understood by referring to FIG. 2 illustrating a block diagram of an exemplary sensor 202 configured to have two selectable sampling rates in accordance with the principles of the disclosure. Sensor 202 may represent any of sensors 102A-D. Sensor 202 comprises an analog section 204 and two analog-to-digital converters, ADC 206A and ADC 206B. The ADCs receive an analog signal representative of a value of the physical parameter sensed by sensor 202 (e.g. acceleration, orientation, magnetic field, altitude or barometric pressure) and convert the analog signal to a digital value which may then be used by sink 104. For the purpose of illustration, let ADC 206A have a fast or high sampling rate, and ADC 206B have a slow or low sampling rate. Those skilled in the art would recognize that such identification is a matter of choice and does not reflect a limitation on an embodiment of sensor 202. ADCs 206A and 206B may be configured to be turned off or otherwise enter a quiescent state in which they consume little or no power via an ADC control signal 208. Control signal 208 may be selectively provided to the ADCs via de-multiplexer (DEMUX) 210. DEMUX 210 may be controlled via rate control 212 which may be a binary signal from rate control generator 110. For example, the illustrative embodiment of FIG. 2 may be configured to select ADC 206A via binary '0' and ADC 206B via binary '1' and the embodiment of rate control generator 110 configured accordingly. However, it would be recognized by those skilled in the art that the configuration is a design choice and not a limitation with respect to the exemplary embodiments. Further, in at least some embodiments, rate control generator 110 may set the control line to the appropriate binary value even if the rate set by generator 108 is more granular. In such an embodiment, the rate control generator 110 may select the ADC, and thereby the sampling rate, by for example, thresholding the sampling rate received from sampling rate generator 108 against a predetermined value as established by the specifications of sensor 202. In addition to controlling the selection of one of ADCs 206A and 206B, rate control 212 may also control the steering of the ADC outputs to sink 104, via multiplexer 214, in the exemplary embodiment of FIG. 2. Further, while two selectable ADCs have been shown in the example embodiment in FIG. 2, in at least some other embodiments a sensor could include more than two such ADCs and thereby increase the granularity of the sampling rate selection. In at least some such embodiments, rate control 212 might comprise a multi-bit binary signal. Note also that while in the example embodiment of FIG. 2, ADC selection and ADC output signal switching has been described in terms of multiplexers, other switching mechanisms may be used and would be appreciated by those of ordinary skill in the art, and such mechanisms would fall within the spirit and scope of the present disclosure. Further, in at least some embodiments, a sensor may include an ADC having a programmable sampling rate provided, for example, by a programmable phase locked loop (PLL). Referring to FIG. 3, there is illustrated therein a block diagram sensor 302 in accordance with such an exemplary embodiment. Sensor 302 may represent any of sensors 102A-D. Sensor 302 comprises an analog section 304 and ADC 306. ADC 306 includes PLL 308 which is configured to receive a rate control signal 310 from rate control generator 110. In at least some embodiments, rate control signal 310 may comprise a multi-bit binary value that programs taps on a programmable divider within PLL 308 (not shown in FIG. 3). The foregoing embodiments are intended to be exemplary and other mechanisms for providing a programmable ADC sampling rate known to those skilled in the art could also be used and would fall within the principles of the disclosure.

Figure 4:
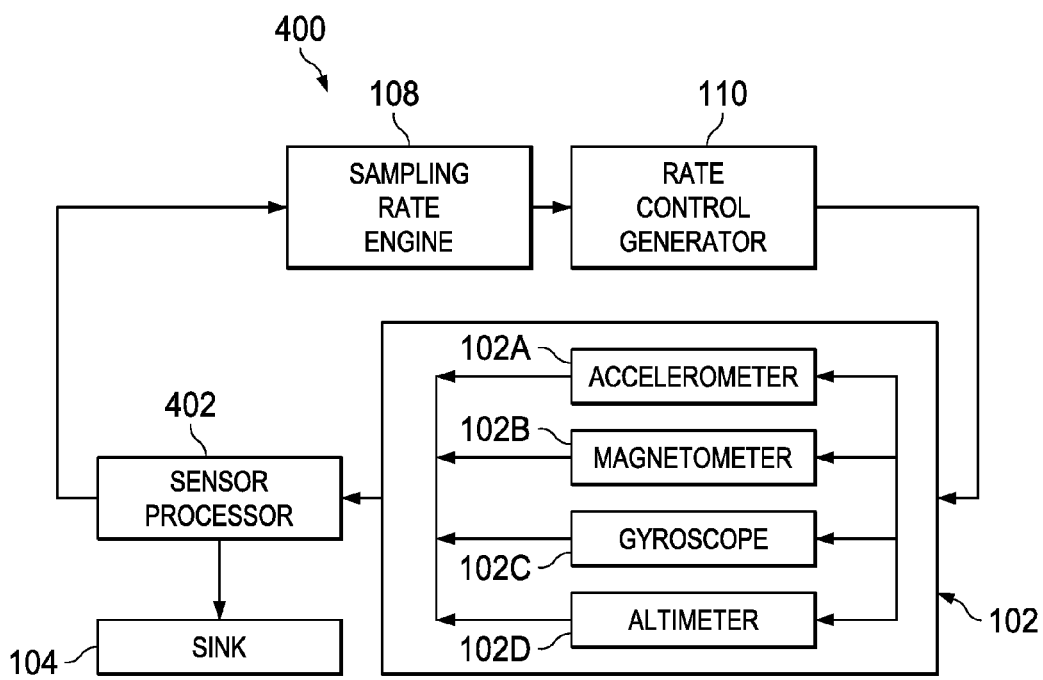
FIG. 4 shows a block diagram of a system in accordance with another embodiment of the disclosure.

Refer now to FIG. 4 illustrating a block diagram of a system 400 for adaptively controlling MEMS sensor sampling rates in accordance with at least some alternative embodiments of the disclosure. System 400 included a plurality of sensors 102, comprising an accelerometer 102A, a magnetometer 102B, a gyro 102C and an altimeter 102D. Output data from the plurality of sensors 102 is coupled to a sensor processor 402. Sensor processor 402 may forward the data as received to sink 104, similar to system 100 in FIG. 1. Further, sensor processor 402 may include dynamic estimation logic (not shown in FIG. 4) which operates analogously to dynamic estimation logic 106 in system 100. As would be appreciated by those skilled in the art, dynamic estimation logic may, in some embodiments be implemented in hardware within sensor processor 402, and in other, alternative, embodiments implemented in software or firmware executed by sensor processor 402. Further, an end user device may use the outputs of multiple sensors to determine a parameter of interest. For example, a navigation application or device may use accelerometer, gyroscope and magnetometer outputs. In at least some embodiments, sensor processor 402 may be used to generate such parameter estimates. Exemplary processes which may be used to estimate particular parameters and which may, in at least some embodiments, be performed at least in part by sensor processor 402 are described below in conjunction with FIGS. 8-9. Sensor processor 402 may, in at least some embodiments be implemented in hardware such as an application specific integrated circuit (ASIC), or, in alternative embodiments, as software of firmware running on a general purpose central processing unit (CPU) or a special purpose processor such as a graphics processing unit (GPU) (for example, using the enhanced floating-point capabilities of such processors).

Figure 5:
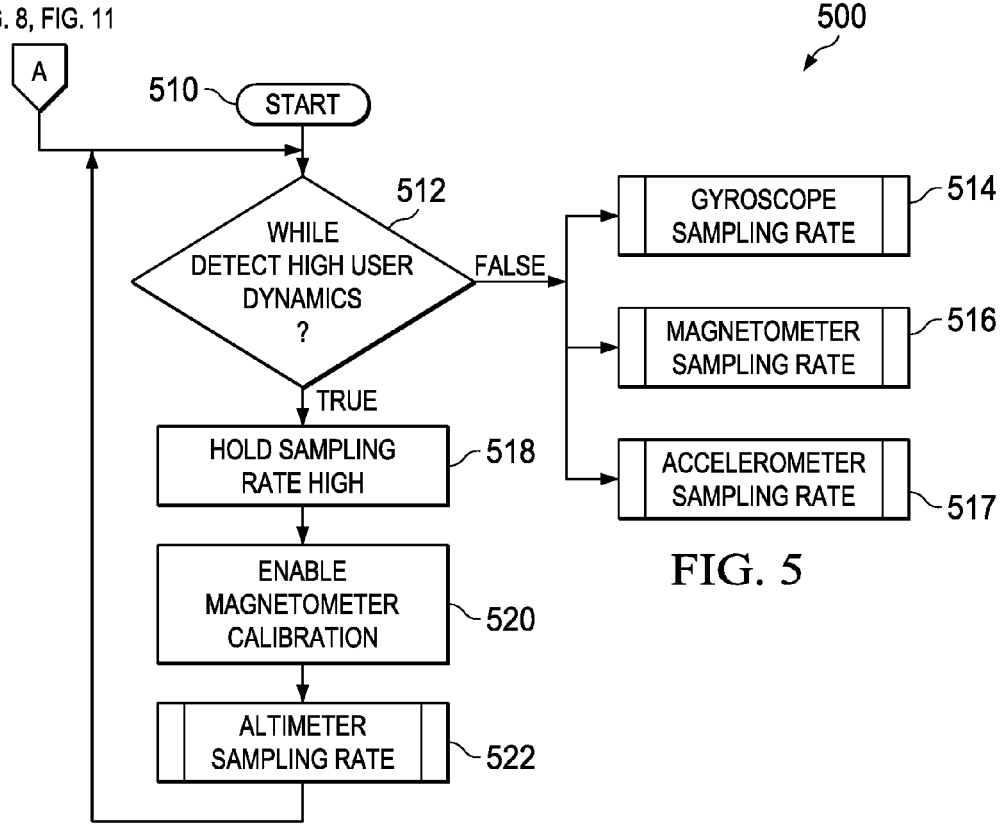
FIG. 5 shows a flowchart of a process in accordance with an embodiment of the disclosure.

To further understand the principles of the disclosure, refer now to FIG. 5 illustrating a flow chart of process 500 for adaptively adjusting sensor sampling rates in accordance with at least some embodiments. At least some portions of process 500 may be performed by sensor processor 402. And, at least some portions of process 500 may be implemented hardware, such as an application specific integrated circuit (ASIC), or as software of firmware running on a general purpose central processing unit (CPU) or a special purpose processor such as a graphics processing unit (GPU) (for example, using the enhanced floating-point capabilities of such processors). Process 500 starts at block 510 and enters a loop via "WHILE" block 512. In block 512, while user dynamics are determined to be high, as for example detected by dynamics estimation logic 106 in an embodiment in accordance with system 100, or sensor processor 402 in an embodiment in accordance with system 400, process 500 loops through the "T" or "true" branch of block 512. On detection of low user dynamics, breaks out of the loop and proceeds via the "F" or "false" branch of block 512 to set or adjust gyro, magnetometer, and/or accelerometer sampling rates in blocks 514, 516 and 517, respectively. Blocks 514, 516 and 517 are described further below. Returning to the "T" branch of block 512, while user dynamics are high, sampling rates are held high, block 518. Additionally, in at least some embodiments, it may be desirable to calibrate a magnetometer when sampling rates are high. And, in particular it may be desirable to calibrate a magnetometer when user dynamics are high whereby the three axes of the magnetometer may all be rotated. In this way, the calibration accuracy is benefited by the high user dynamics and high sampling rate. Thus, in block 520, magnetometer calibration is enabled while high user dynamics are high. An alternative mechanism, which may be used when sensor calibration during low user dynamics is desirable, is discussed below in conjunction with the adjusting of gyro sampling rates, block 514, now considered.

Figure 6:
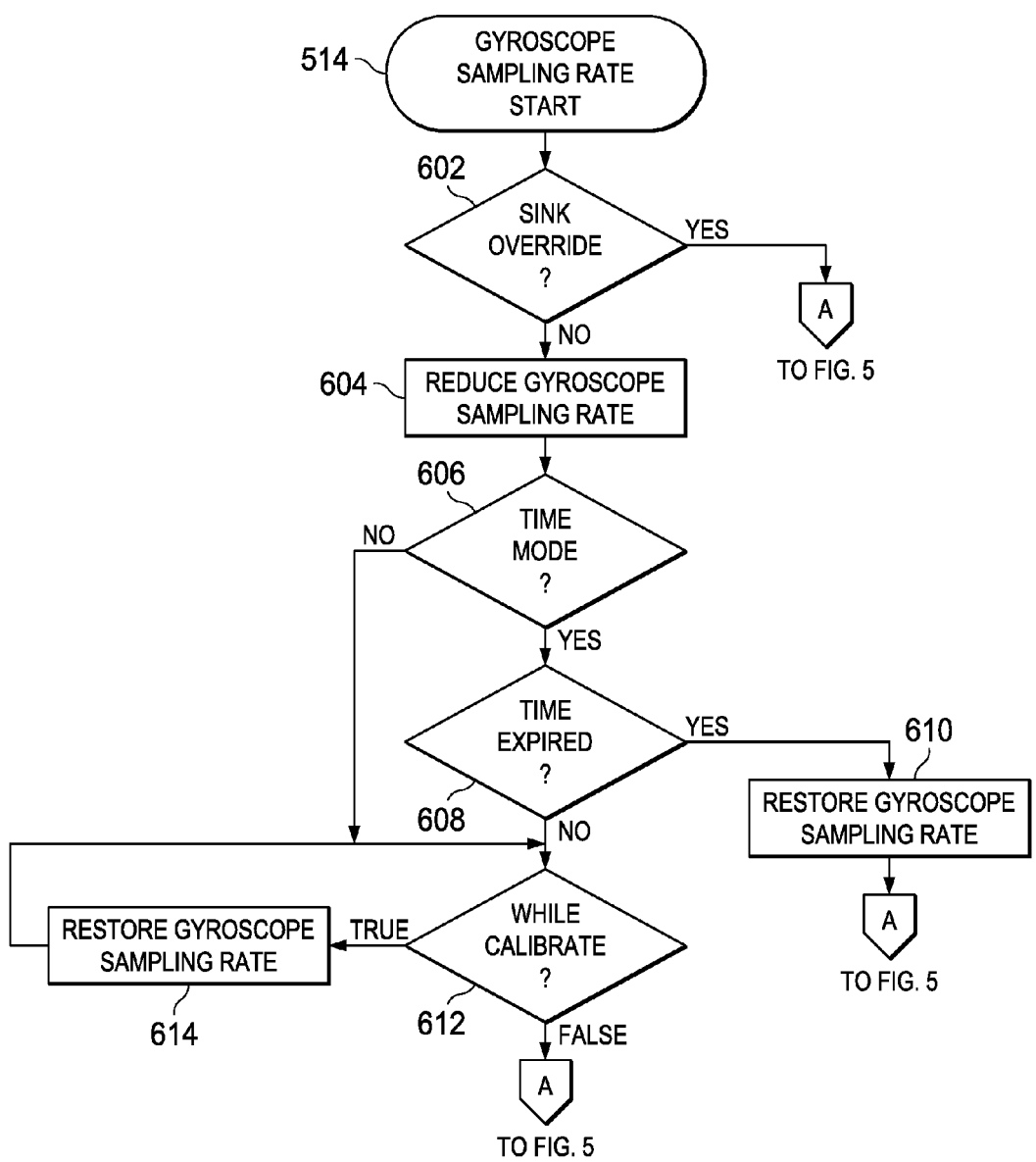
FIG. 6 shows in further detail a flowchart of a portion of the process of FIG. 5.

Referring to FIG. 6, there is illustrated therein a process for adaptively adjusting a gyro sampling rate, block 514, in further detail. As would be understood by those skilled in the art, in at least some embodiments, all of portions of block 514 may be implemented in hardware, such as an application specific integrated circuit (ASIC) or in at least some alternative embodiments as software or firmware running on, for example, sensor processor 402 or a general purpose central processing unit (CPU) (not shown) in the device employing the plurality of sensors 102.

In decision block 602, gyro sampling rate process 514 determines if the low user dynamics detected in block 512 is overridden. If a device or application that uses output from the gyro, represented in exemplary systems 100 and 400, by sink 104, requires gyro data at a high sampling rate regardless or independent of user dynamics. In at least some embodiments such a device or application may assert an override that may be detected in decision block 602. If such an override is asserted process 514 returns to block 512. Even if low user dynamics persists, by looping through the "F" branch of block 512 and blocks 514 and 602, the gyro sampling rate may be maintained until the device or application de-asserts its override.

If no override has been asserted or a previously asserted override is de-asserted, block 602 falls through the "No" branch, and in block 604, the gyro sampling rate is reduced. In at least some embodiments in accordance with system 100, block 604 may be performed, at least in part, by dynamics estimation logic 106, sampling rate engine 108 and rate control generator 110. Similarly, in at least some embodiments in accordance with system 400, block 604 may be performed, at least in part, by sensor processor 402, sampling rate engine 108 and rate control generator 110.

In at least some embodiments, it may be desirable to maintain a reduced sampling rate for a predetermined or preselected time interval. For example, if one or more of the plurality of sensors is used to detect when the end-user device is stationary, the sampling rate may be reduced (or turned off) for a predetermined time interval and then restored to sense if the end-user device is still stationary. Thus, if for the purpose of illustration, if an acceptable latency in sensing if the device is stationary is 1 second, the sensors might be turned off for 900 milliseconds (ms) and then turned on to use the last 100 ms to sense if the device is still stationary. If such a time mode is provided, block 606 proceeds by the "Yes" branch to block 608. Otherwise, block 606 proceeds to block 612, described below, via the "No" branch. Returning to decision block 608, it is determined if the aforementioned predetermined or preselected time interval is expired. If yes, decision block 608 proceeds to block 610 and the sampling rate is restored to its pre-reduction value and gyro rate process 514 returns to block 512. Otherwise, if the time interval has not expired, decision block 608 proceeds to block 612.

In at least some embodiments, blocks 612 and 614 provide for calibration of a gyro during instances of low user dynamics. In some embodiments, it may be desirable to calibrate a gyro sensor at low user dynamics. However, calibration may, in many, if not most embodiments benefit from a high sampling rate. The high number of samples provided thereby increase calibration accuracy. Thus, in block 612, if a gyro sensor is being calibrated during an instance of low user dynamics, via the "T" branch, the gyro sampling rate is restored to a high value in block 614, and the high sampling rate is maintained while the calibration proceeds via the loop in decision block 612. In at least some embodiments, calibration may proceed until user dynamics are no longer low. When calibration is complete (WHILE (calibrate)=FALSE), decision block 612 returns to block 512 by the "F" branch. If upon return to block 512, user dynamics are low, block 512 proceeds via the "F" branch back to block 514 where the gyro sampling rate may be reduced, reflecting the low user dynamics via blocks 602 and 604.

Figure 7:
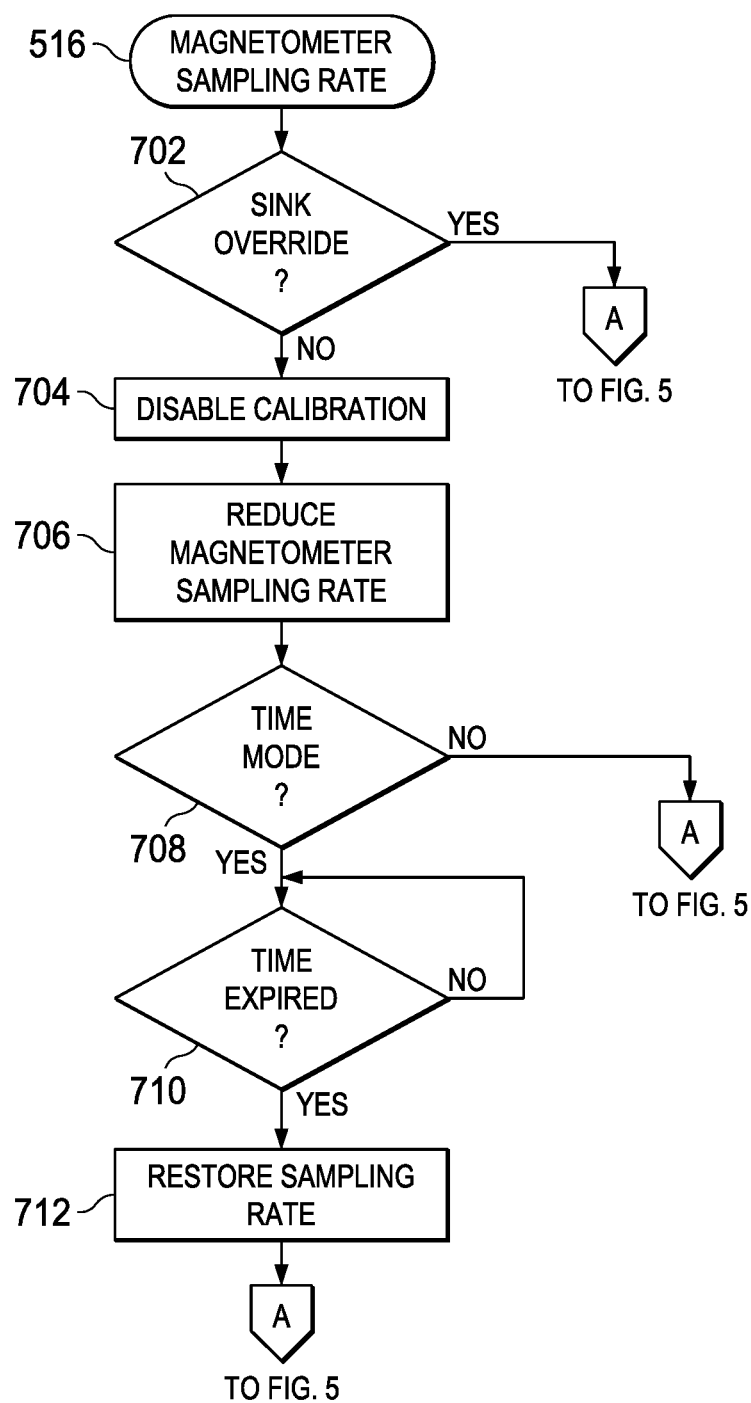
FIG. 7 shows in further detail a flowchart of another portion of the process of FIG. 5.

Returning to FIG. 5, while user dynamics are low, block 512, in at least some embodiments the magnetometer sensor sampling rate may also be adjusted, block 516. FIG. 7 illustrates a process 516 for adaptively adjusting a magnetometer sampling rate in accordance with at least some embodiments of the disclosure.

In decision block 702 it is determined if a device or application that uses output from the magnetometer, represented in exemplary systems 100 and 400 by sink 104, requires magnetometer data at a high sampling rate has asserted a signal to override reduction of the magnetometer sampling rate. Block 702 is analogous to block 602, FIG. 6 with respect to the magnetometer sampling rate. If such an override is asserted process 516 returns to block 512, and the magnetometer sampling rate remains high. As described above in conjunction with block 602, even if low user dynamics persists, by looping through the "F" branch of block 512 and blocks 516 and 702, the magnetometer sampling rate may be maintained until the device or application de-asserts its override.

If no override has been asserted or a previously asserted override is de-asserted, block 702 falls through the "No" branch, and in block 704, magnetometer calibration is disabled. Recall, as previously described above, in at least some embodiments, it may be desirable to calibrate a magnetometer when user dynamics are high. Block 520, FIG. 5 provides for magnetometer calibration when user dynamics are high. Moreover, as would be appreciated by those skilled in the art, in alternative embodiments in which magnetometer calibration may be performed or desired when user dynamics are low, a calibration mechanism paralleling blocks 612 and 614, FIG. 6 may be used, and such embodiments would fall within the principles disclosed herein.

Continuing, in block 706, the magnetometer sampling rate is reduced. In at least some embodiments in accordance with system 100, block 604 may be performed, at least in part, by dynamics estimation logic 106, sampling rate engine 108 and rate control generator 110. Similarly, in at least some embodiments in accordance with system 400, block 706 may be performed, at least in part, by sensor processor 402, sampling rate engine 108 and rate control generator 110.

Similar to process 514 with respect to adaptive adjustment of the gyro sampling rate, in at least some embodiments, process 516 may reduce the magnetometer sampling rate for a predetermined or preselected time interval. An example of such use has been described above in conjunction with FIG. 6. Thus, in block 708, it is determined if the sampling rate is to be reduced for a predetermined time interval (time mode). If not, process 516 returns to block 512 via the "No" branch and while user dynamics are low, the magnetometer sampling rate is maintained at a low value via the "F" branch of block 512, block 516, the "No" branch of block 702 and block 706. If, however, in block 708 it is determined that the sampling rate is to be reduced for a predetermined time interval, block 710 loops until the predetermined time interval expires. On expiry of the time interval, block 710 breaks out of the loop via the "Yes" branch and in block 712, the sampling rate is restored to a high value. Process 516 then returns to block 512.

Figure 8:
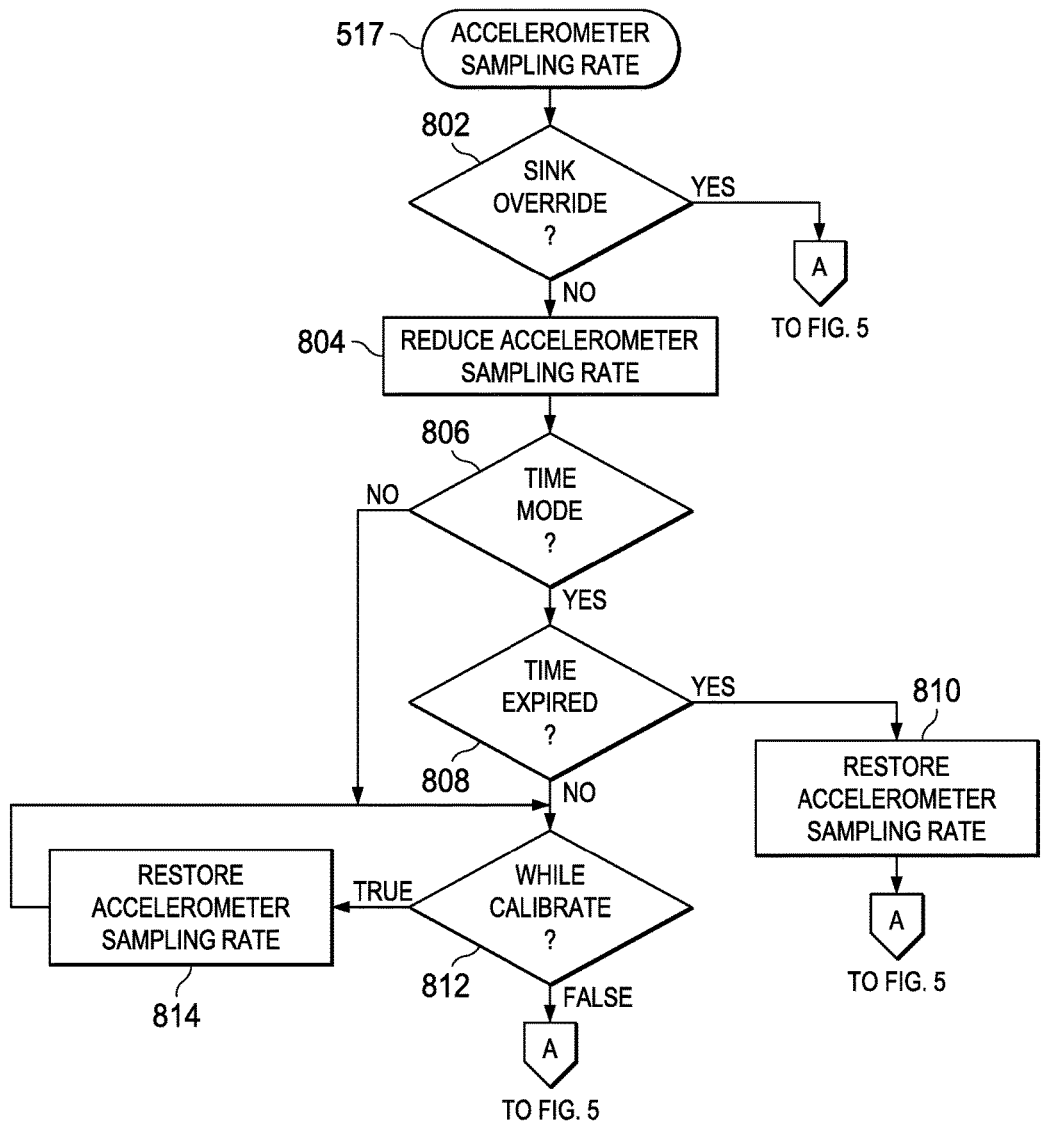
FIG. 8 shows in further detail a flowchart of yet another portion of the process of FIG. 5.

Returning to FIG. 5, while user dynamics are low, block 512, in at least some embodiments the accelerometer sensor sampling rate may also be adjusted, block 517. In at least some embodiments, the power consumption of the accelerometer may be sufficiently low that it may be advantageous to omit adaptively reducing the accelerometer sampling rate. In other embodiments, it may be desirable to adaptively reduce the sampling rate of the accelerometer. Referring to FIG. 8, there is illustrated therein a process for adaptively adjusting an accelerometer sampling rate, block 517, in further detail. As would be understood by those skilled in the art, in at least some embodiments, all of portions of block 517 may be implemented in hardware, such as an application specific integrated circuit (ASIC) or in at least some alternative embodiments as software or firmware running on, for example, sensor processor 402 or a general purpose central processing unit (CPU) (not shown) in the device employing the plurality of sensors 102.

In decision block 802, accelerometer sampling rate process 517 determines if the low user dynamics detected in block 512 is overridden. If a device or application that uses output from the accelerometer, represented in exemplary systems 100 and 400, by sink 104, requires accelerometer data at a high sampling rate regardless or independent of user dynamics. In at least some embodiments such a device or application may assert an override that may be detected in decision block 802. If such an override is asserted process 517 returns to block 512. Even if low user dynamics persists, by looping through the "F" branch of block 512 and blocks 517 and 802, the accelerometer sampling rate may be maintained until the device or application de-asserts its override.

If no override has been asserted or a previously asserted override is de-asserted, block 802 falls through the "No" branch, and in block 804, the accelerometer sampling rate is reduced. In at least some embodiments in accordance with system 100, block 804 may be performed, at least in part, by dynamics estimation logic 106, sampling rate engine 108 and rate control generator 110. Similarly, in at least some embodiments in accordance with system 400, block 804 may be performed, at least in part, by sensor processor 402, sampling rate engine 108 and rate control generator 110.

In at least some embodiments, it may be desirable to maintain a reduced sampling rate for a predetermined or preselected time interval. An example of such use has been described above in conjunction with FIG. 6. If such a time mode is provided, block 806 proceeds by the "Yes" branch to block 808. Otherwise, block 806 proceeds to block 812, described below, via the "No" branch. Returning to decision block 808, it is determined if the aforementioned predetermined or preselected time interval is expired. If yes, decision block 808 proceeds to block 810 and the sampling rate is restored to its pre-reduction value and accelerometer rate process 517 returns to block 512. Otherwise, if the time interval has not expired, decision block 808 proceeds to block 812.

In at least some embodiments, blocks 812 and 814 provide for calibration of an accelerometer during instances of low user dynamics. In some embodiments, it may be desirable to calibrate an accelerometer sensor at low user dynamics. However, calibration may, in many, if not most embodiments benefit from a high sampling rate. The high number of samples provided thereby increase calibration accuracy. Thus, in block 812, if an accelerometer is being calibrated during an instance of low user dynamics, via the "T" branch, the accelerometer sampling rate is restored to a high value in block 814, and the high sampling rate is maintained while the calibration proceeds via the loop in decision block 812. In at least some embodiments, calibration may proceed until user dynamics are no longer low. When calibration is complete (WHILE(calibrate)=FALSE), decision block 812 returns to block 512 by the "F" branch. If upon return to block, user dynamics are low, block 512 proceeds via the "F" branch back to block 517 where the accelerometer sampling rate may be reduced, reflecting the low user dynamics via blocks 802 and 804.

Figure 9:
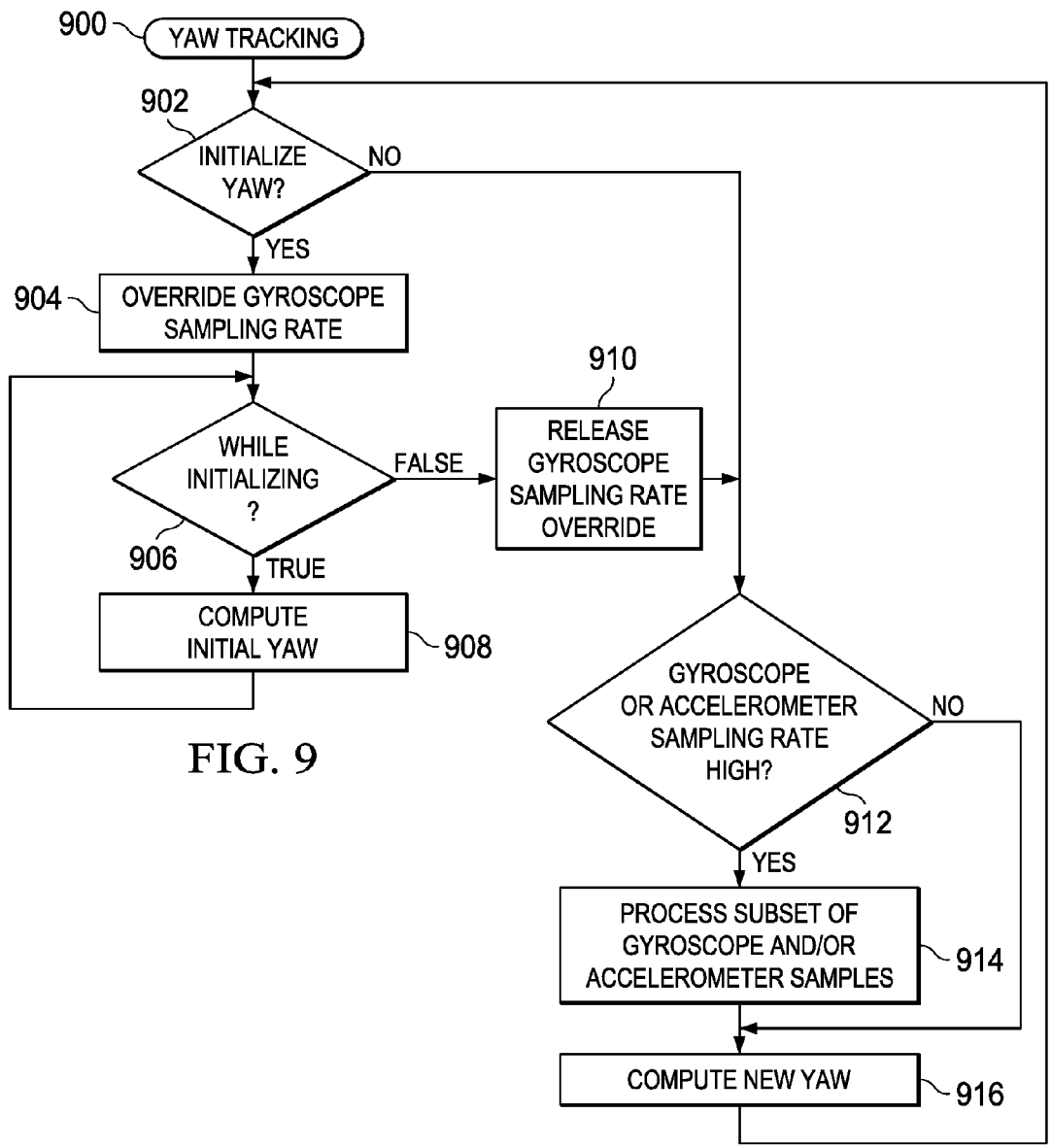
FIG. 9 shows a flowchart of a process in accordance with another embodiment of the disclosure.

As described above, an application may override the reduction of a sensor sampling rate that might otherwise be instantiated based on the user dynamics. Consider, as an example, yaw which for the purpose of the disclosure is the difference or deviation of the user's direction of motion relative to the direction the user device is pointing. Thus, the direction the user is heading may be determined by adjusting the heading of the user's device by the yaw angle. Typically, once initialized, yaw may be tracked at a reduced sampling rate inasmuch as yaw generally varies slowly. During initialization of the yaw, however, it may be desirable to maintain sensor sampling rates at a high value. An exemplary yaw tracking process 900 in accordance with at least some embodiments is shown in FIG. 9. Yaw tracking process 900 may be performed, at least in part by sensor processor 402, for example as software or firmware running thereon, or alternatively on a general purpose CPU, or in yet another alternative, as application specific hardware implemented in sensor processor 402 or, in still another alternative, as a discrete ASIC.

If the yaw is being initialized, block, 902, process 900 may, in block 904, override the gyro sampling rate as otherwise may be determined based on user dynamics as described above in conjunction with FIG. 5. In this way, a high gyro sampling rate may be maintained for the purpose of initializing the yaw value. In block 906, process 900 loops while the initial value of the yaw is computed in block 908. The initial value of the yaw may be determined using a magnetic heading from the magnetometer data and a coarse location determination. As would be recognized by those skilled in the art, a coarse location may be obtained, for example, in a smartphone embodiment by triangulation from a plurality of cell towers. Alternatively, embodiments equipped with GPS may obtain location data therefrom. Using the location data, a magnetic declination angle for the particular location may be computed using algorithms known in the art. The yaw may then be determined using magnetometer data corrected for the declination of the Earth's magnetic field at the location of the end-user device. Upon completion of the initialization, process 900 breaks out of the loop in block 906 and releases the gyro sampling rate override in block 910.

If, in block 902, the yaw is not being initialized (or upon completion of the initialization and release of the gyro sampling rate at block 810), the yaw sampling rate is set in blocks 912 and 914. If, in block 912, the gyro and accelerometer sampling rates are low, as for example, determined by low user dynamics in accordance with the principles of the disclosure, block 912 proceeds by the "No" branch and a new yaw value is computed, block 916. A new yaw value may be computed by using the initial or previously determined yaw and an integration of gyro and accelerometer data to determine a current angular position offset from an initial or prior angular position. Briefly, in at least some embodiments, such as a hand-held device as describe in the in the related U.S. patent application Ser. No. 13/023,987 for "ACCELEROMETER-AIDED GYROSCOPE" referenced above, the orientation of the device with respect to ground can vary depending on how the user is holding the device. In such embodiments, the updated angular positions from the gyro measurements may be used to transform the magnetometer data, which is in the magnetometer sensor's reference frame into a local East, North, Up (ENU) frame. This so-called de-tilted magnetometer data may then be used to compute the yaw angle. If $m_x$ and $m_y$ denote the de-tilted magnetometer data in the "E" and "N" directions respectively, then the yaw angle, y, may be determined by:

$$y = \arctan(m_x/m_y) - d \qquad (1)$$

where d denotes the declination angle at the location of the end user device. Suitable techniques for the numerical integration of data are known in the art, and it would be appreciated by those skilled in the art that such techniques are themselves based on discrete data samples. Returning to block 912, if either the gyro sampling rate, accelerometer sampling rate or both are high, for example if user dynamics is high, process 900 may, in block 914, process a subset of the gyro data samples. Recall that, although user dynamics might be high, the yaw, in at least some embodiments, may be slowly varying and yaw tracking may not need to use all of the gyro samples generated at the high gyro sampling rate. In other words, process 900 at block 914 subsamples the gyro data and, in block 916 computes the new yaw value based on the subsampled gyro and/or accelerometer data.

Figure 10:
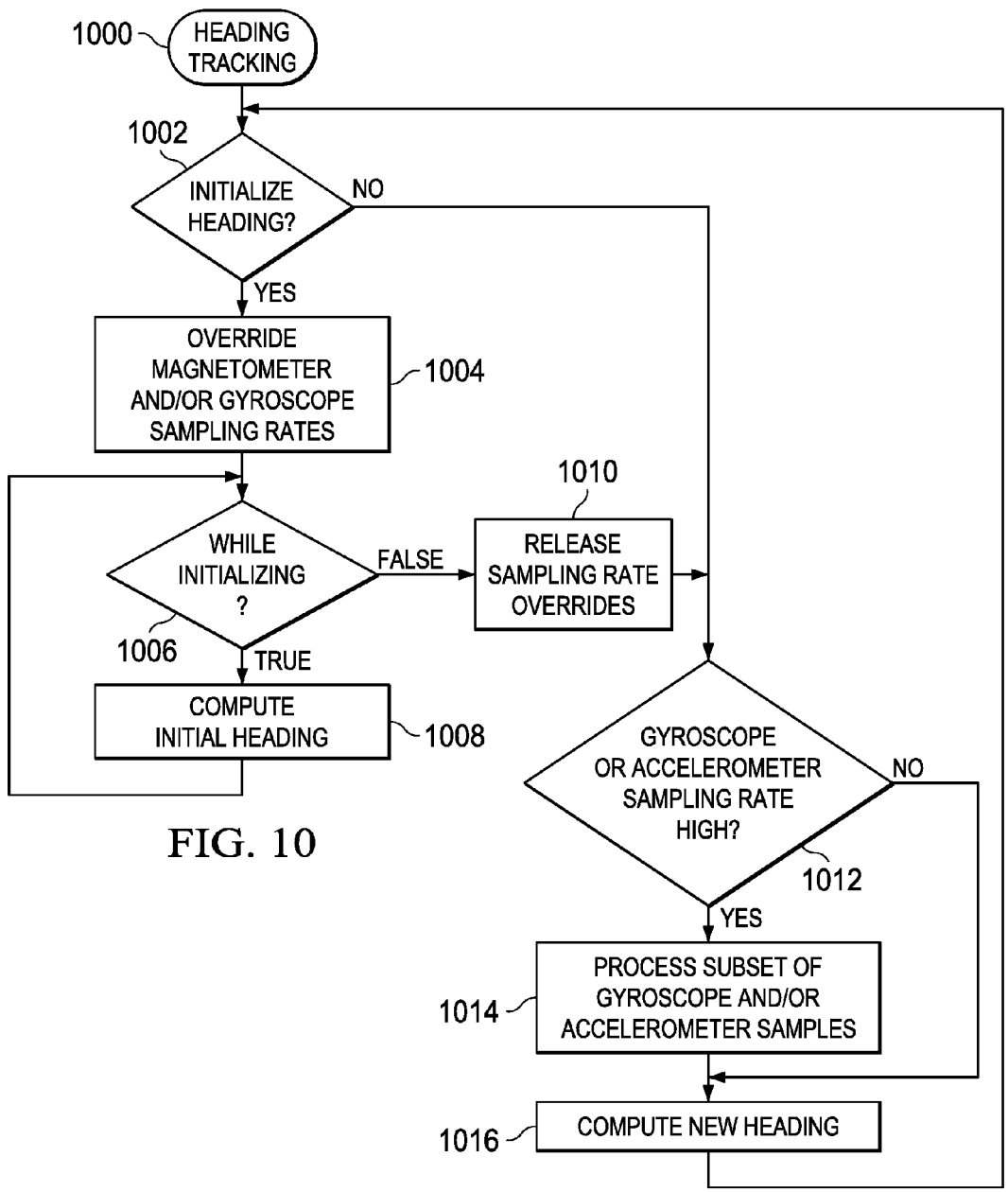
FIG. 10 shows a flowchart of a process in accordance with still another embodiment of the disclosure.

Similarly to the yaw, heading values may, in at least some embodiments, be tracked at reduced sampling rate. Refer now to FIG. 10 illustrating a process 1000 for heading tracking in accordance with at least some embodiments of the disclosure. Heading tracking process 1000 may be performed, at least in part by sensor processor 402, for example as software or firmware running thereon, or alternatively on a general purpose CPU, or in yet another alternative, as application specific hardware implemented in sensor processor 402 or, in still another alternative, as a discrete ASIC. Heading tracking may use data from a combination of the magnetometer, gyro and accelerometer.

If the heading is being initialized, block, 1002, process 1000 may, in block 1004, override the magnetometer and/or gyro sampling rates as otherwise may be determined based on user dynamics as described above in conjunction with FIG. 5. (Recall, that in accordance with at least some embodiments, the sampling rates of some sensors may be reduced while the sampling rates of other sensors may remain high.) In this way, high magnetometer and gyro sampling rates may be maintained for the purpose of initializing the heading value. In block 1006, process 1000 loops while the initial value of the heading is computed in block 1008. The initial value of the heading may be determined using magnetometer data. Upon completion of the initialization, process 1000 breaks out of the loop in block 1006 and releases the magnetometer sampling rate and/or gyro sampling rate override in block 1010.

If, in block 1002, the heading is not being initialized (or upon completion of the initialization and release of the gyro sampling rate at block 1010), the heading sampling rate is set in blocks 1012 and 1014. If, in block 1012, the gyro sampling rate and accelerometer sampling rate are low, as for example, determined by low user dynamics in accordance with the principles of the disclosure, block 1012 proceeds by the "No" branch and a new heading value is computed, block 1016. A new heading value may be computed by using the initial or previously determined heading and an integration of gyro data and accelerometer data to determine a current heading offset from an initial or prior heading. Techniques for the numerical integration of data are known in the art, and it would be appreciated by those skilled in the art that such techniques are themselves based on discrete data samples. Returning to block 1012, if either the accelerometer or gyro sampling rate, or both are high, for example if user dynamics is high, process 1000 may, in block 1014, process a subset of the accelerometer and/or gyro data that has been sampled at the high rate. Recall that, although user dynamics might be high, the heading, in at least some embodiments, may be slowly varying and heading tracking may not need to use all of the gyro and accelerometer samples generated at the high sampling rate. In other words, process 1000 at block 1014 subsamples the gyro and/or accelerometer data and, in block 1016 computes the new heading value based on the subsampled gyro and/or accelerometer data.

Figure 11:
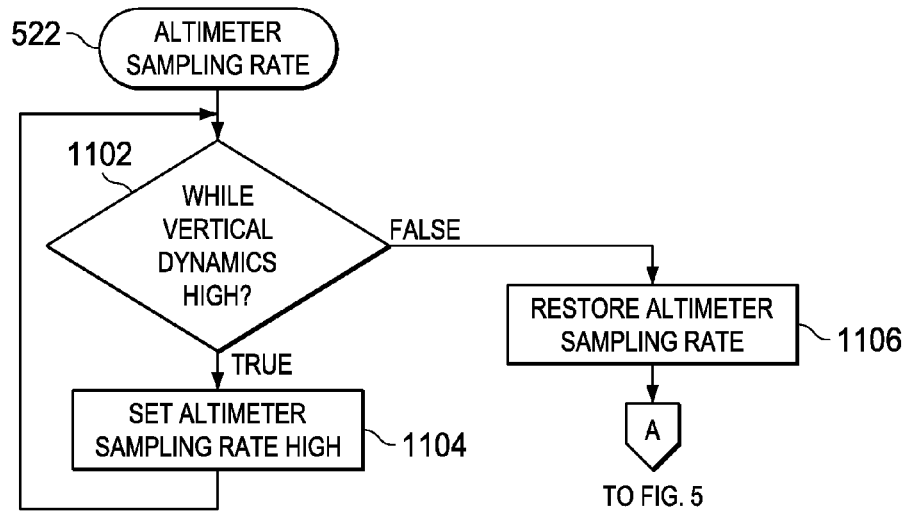
FIG. 11 shows a flowchart of a process in accordance with still another embodiment of the disclosure.

Returning to FIG. 5, in at least some embodiments, it may be desirable to adjust the altimeter sampling rate, block 522. (The altimeter may equivalently be referred to a barometer or a pressure sensor.) For example, if high user dynamics in the vertical direction are detected by the accelerometer, it may be desirable to increase the altimeter sampling rate over a lower, perhaps default, value. Thus, by way of further example, to track the floor that an elevator car is on, it may be desirable to sample the altimeter at a high sampling rate. A process for adaptively adjusting an altimeter sampling rate, block 522, is shown in further detail in FIG. 11. As would be understood by those skilled in the art, in at least some embodiments, all of portions of block 522 may be implemented in hardware, such as an application specific integrated circuit (ASIC) or in at least some alternative embodiments as software or firmware running on, for example, sensor processor 402 or a general purpose central processing unit (CPU) (not shown) in the device employing the plurality of sensors 102. If high vertical dynamics are sensed, process 522 loops via "WHILE" block 1102, and in block 1104 sets, via the "T" branch of block 1102, a sampling rate of the altimeter to a high value, which may be, for example, selected from a predetermined set of values as described above in conjunction with FIG. 1. Upon the return of vertical dynamics to a low value, process 522 breaks out of the "WHILE" loop via the "F" branch of block 1102. In block 1106 the sampling rate of the altimeter is restored to a low value, which may, in at least some embodiments be a default value.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A system comprising:
   a plurality of sensors;
   a sensor processor coupled to an output of each sensor of the plurality of sensors, the sensor processor estimating user dynamics in response to a first output signal of a first sensor of the plurality of sensors; and
   a sampling rate engine coupled to an output of the sensor processor, the sampling rate engine determining a sampling rate value of a second sensor of the plurality of sensors in response to a user dynamics value from the sensor processor, wherein the sensor processor is configured to set a respective calibration sampling rate for each sensor of the plurality of sensors, and
   wherein the second sensor comprises a selectable sampling rate, the selectable sampling rate configured in response to the sampling rate value determined by the sampling rate engine.

2. The system of claim 1, further comprising a rate control generator configured to receive the sampling rate value determined by the sampling rate engine and coupled to the second sensor, wherein the selectable sampling rate is selected in response to an output of the rate control generator, the output of the rate control generator determined in response to the sampling rate value.

3. The system of claim 1, wherein the second sensor comprises a first ADC and a second ADC, and wherein the selectable sampling rate comprises selecting one of a sampling rate of the first ADC and a sampling rate of the second ADC.

4. The system of claim 1 wherein the sensor processor is configured to estimate a physical parameter using sensor data from at least two sensors of the plurality of sensors.

5. The system of claim 1, wherein the sensor processor estimates user dynamics with an accelerometer.

6. The system of claim 1, wherein the sensor processor estimates user dynamics with an altimeter.

7. The system of claim 1, wherein the plurality of sensors comprises one of a magnetometer and a gyroscope.

* * * * *